(12) United States Patent
Yuen et al.

(10) Patent No.: US 10,289,206 B2
(45) Date of Patent: May 14, 2019

(54) FREE-FORM DRAWING AND HEALTH APPLICATIONS

(71) Applicant: Intel Corporation, Santa Clara, CA (US)

(72) Inventors: Kathy Yuen, Portland, OR (US); Lenitra M. Durham, Beaverton, OR (US); Giuseppe Raffa, Portland, OR (US); Glen J. Anderson, Beaverton, OR (US); Daniel S. Lake, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 627 days.

(21) Appl. No.: 14/975,362

(22) Filed: Dec. 18, 2015

(65) Prior Publication Data

US 2017/0177086 A1    Jun. 22, 2017

(51) Int. Cl.
| | | |
|---|---|---|
| *G06F 17/30* | (2006.01) | |
| *G01C 21/36* | (2006.01) | |
| *G01C 21/20* | (2006.01) | |
| *G06F 3/0346* | (2013.01) | |
| *G06F 3/0484* | (2013.01) | |
| *G06F 3/01* | (2006.01) | |
| *G06F 3/03* | (2006.01) | |
| *A61B 5/00* | (2006.01) | |
| *G06F 16/435* | (2019.01) | |

(Continued)

(52) U.S. Cl.
CPC .............. *G06F 3/017* (2013.01); *A61B 5/681* (2013.01); *G01C 21/20* (2013.01); *G01C 21/3664* (2013.01); *G06F 3/014* (2013.01); *G06F 3/0304* (2013.01); *G06F 3/0346* (2013.01); *G06F 3/04847* (2013.01); *G06F 16/436* (2019.01); *A63B 22/0076* (2013.01); *A63B 22/02* (2013.01); *A63B 22/0605* (2013.01); *A63B 24/0087* (2013.01); *A63B 69/0028* (2013.01); *A63B 69/16* (2013.01); *A63B 71/0622* (2013.01); *A63B 2071/0625* (2013.01); *A63B 2071/0636* (2013.01); *A63B 2220/12* (2013.01); *A63B 2220/40* (2013.01); *A63B 2220/806* (2013.01); *A63B 2220/807* (2013.01); *A63B 2220/833* (2013.01); *A63B 2220/836* (2013.01); *A63B 2225/50* (2013.01)

(58) Field of Classification Search
CPC ............................... G06F 3/017; G06F 3/0346
See application file for complete search history.

(56) References Cited

U.S. PATENT DOCUMENTS 7,456,815 B2 * 11/2008 Reime ................... G06F 3/0346
                                                         345/204
9,489,125 B2 * 11/2016 Tu ........................ G06F 3/04883
(Continued)

*Primary Examiner* — William L Bashore
*Assistant Examiner* — Nathan K Shrewsbury
(74) *Attorney, Agent, or Firm* — Schwegman Lundberg & Woessner, P.A.

(57) ABSTRACT

Various systems and methods for implementing free-form drawing for health applications are described herein. A system for implementing a health application includes a user interface module to receive, at a user device, a plurality of parameters including a free-form gesture path, the free-form gesture path representing an air gesture performed by a user of the user device; and a control module to adjust a fitness routine of the user based on the plurality of parameters.

24 Claims, 6 Drawing Sheets

(51) Int. Cl.
*A63B 71/06* (2006.01)
*A63B 22/00* (2006.01)
*A63B 22/02* (2006.01)
*A63B 22/06* (2006.01)
*A63B 24/00* (2006.01)
*A63B 69/00* (2006.01)
*A63B 69/16* (2006.01)

(56) References Cited

U.S. PATENT DOCUMENTS

| | | | | |
|---|---|---|---|---|
| 9,812,104 | B2* | 11/2017 | Seo | G10H 1/0091 |
| 2004/0032410 | A1* | 2/2004 | Ryan | G06T 15/20 |
| | | | | 345/427 |
| 2007/0219050 | A1* | 9/2007 | Merril | A63B 22/14 |
| | | | | 482/1 |
| 2009/0233769 | A1* | 9/2009 | Pryor | B60K 35/00 |
| | | | | 482/8 |
| 2010/0295783 | A1* | 11/2010 | El Dokor | G06F 3/017 |
| | | | | 345/158 |
| 2011/0022308 | A1* | 1/2011 | Britton | G01C 21/3664 |
| | | | | 701/533 |
| 2011/0242305 | A1* | 10/2011 | Peterson | G01S 15/003 |
| | | | | 348/77 |
| 2012/0119988 | A1* | 5/2012 | Izumi | G06F 3/017 |
| | | | | 345/156 |
| 2012/0319989 | A1* | 12/2012 | Argiro | G06F 3/038 |
| | | | | 345/174 |
| 2013/0004016 | A1* | 1/2013 | Karakotsios | G06K 9/00355 |
| | | | | 382/103 |
| 2013/0180385 | A1* | 7/2013 | Hamilton | G10H 1/0016 |
| | | | | 84/603 |
| 2013/0297201 | A1* | 11/2013 | Van Hende | G01C 21/3407 |
| | | | | 701/425 |
| 2014/0055352 | A1* | 2/2014 | Davis | G06F 3/017 |
| | | | | 345/156 |
| 2014/0063055 | A1* | 3/2014 | Osterhout | G06F 3/005 |
| | | | | 345/633 |
| 2014/0129976 | A1* | 5/2014 | Beaurepaire | G01C 21/367 |
| | | | | 715/788 |
| 2014/0168100 | A1* | 6/2014 | Argiro | G06F 3/0416 |
| | | | | 345/173 |
| 2014/0184496 | A1* | 7/2014 | Gribetz | G02B 27/017 |
| | | | | 345/156 |
| 2014/0274379 | A1* | 9/2014 | Justice | A63F 13/12 |
| | | | | 463/31 |
| 2014/0282276 | A1* | 9/2014 | Drucker | G06F 17/245 |
| | | | | 715/863 |
| 2014/0320615 | A1* | 10/2014 | Kuribayashi | G09G 3/003 |
| | | | | 348/54 |
| 2015/0348429 | A1* | 12/2015 | Dalal | G09B 5/06 |
| | | | | 434/258 |
| 2016/0062471 | A1* | 3/2016 | Wang | G06F 3/017 |
| | | | | 345/156 |
| 2016/0196042 | A1* | 7/2016 | Laute | G06F 3/017 |
| | | | | 715/845 |
| 2017/0039480 | A1* | 2/2017 | Bitran | G06F 19/345 |

* cited by examiner ific details.

FREE-FORM DRAWING AND HEALTH APPLICATIONS

TECHNICAL FIELD

Embodiments described herein generally relate to user interfaces and in particular, to improving map and navigation applications.

BACKGROUND

Mobile devices have become prevalent in everyday use. People who exercise are able to take advantage of mobile devices to assist in their workouts. Fitness applications that run on mobile devices may be used to track progress, display reminders, provide workout advice, or share experiences with others.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

In the following description, for purposes of explanation, numerous specific details are set forth in order to provide a thorough understanding of some example embodiments. It will be evident, however, to one skilled in the art that the present disclosure may be practiced without these specific details.

Positioning systems, such as the Global Positioning System (GPS), provide signals to receivers, which allow the receivers to calculate a position on Earth using trilateration. GPS was originally developed for the U.S. Department of Defense for military and strategic uses. A mechanism called Selective Availability was used to introduce errors so that civilian navigation signals were significantly less accurate than military. In 2000, the Selective Availability mechanism was disabled and GPS signals available to the civilian population became as accurate as those available to military. This highly accurate positioning system, coupled with an influx of mobile devices, allowed for many location-based services to evolve. One popular use of positioning systems, such as GPS and GLONASS (Global Navigation Satellite System), is for navigation. With electronic maps, processes to determine potential routes from an origin to a destination, and precise locations, mapping and navigation systems became readily affordable and available for the masses. In more current mobile devices, such as smart phones, maps and navigation applications are bundled with the mobile device and may interact with, or be incorporated with, health-related applications executing on the mobile device.

Some health-related apps allow users to select routes that have been previously used by other users and are usually organized by distance and elevation change. However, such apps may not provide an easy mechanism to search for or plan routes using these metrics (e.g., distance and elevation). Systems and methods described herein relate to using free-form drawing (e.g., air gestures) as query criteria to individually tailor routes to the specific types of paths that user might want to take.

Figure 1:
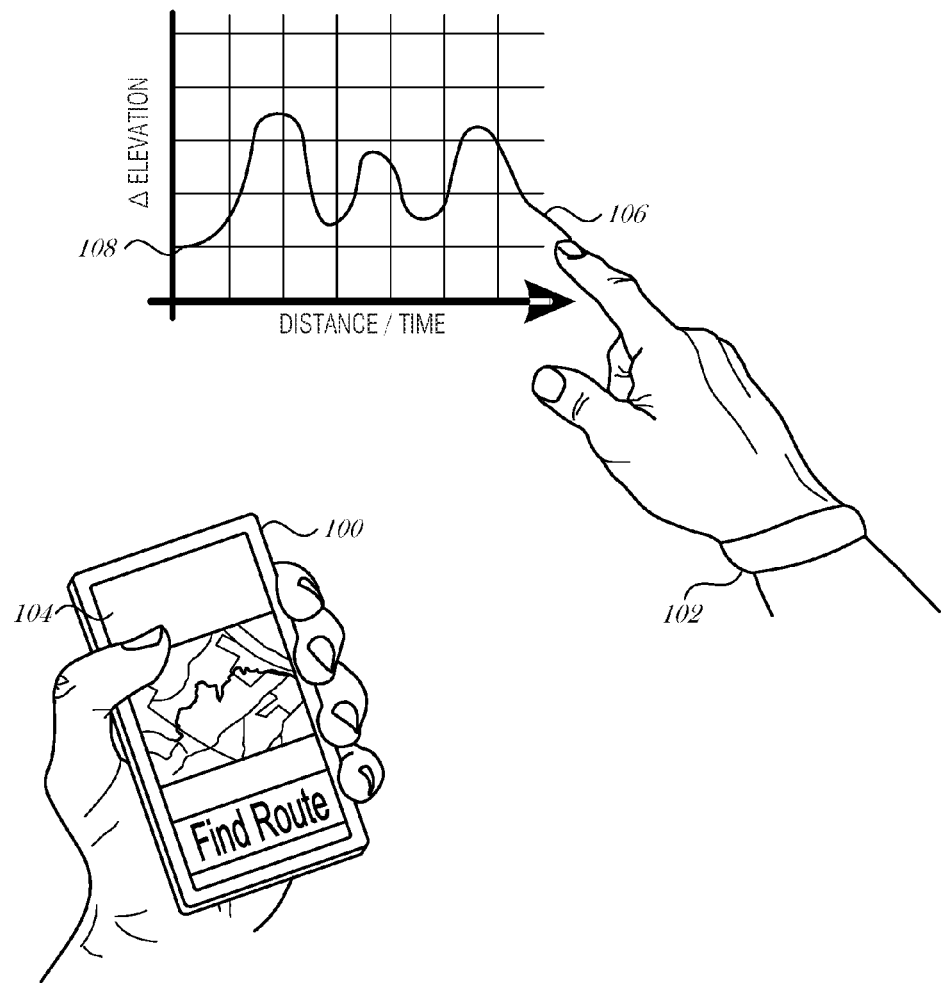
FIG. 1 is a diagram illustrating an example usage, according to an embodiment.

FIG. 1 is a diagram illustrating an example usage, according to an embodiment. In the example illustrated in FIG. 1, a user is holding a mobile device 100 and is wearing a wearable device 102. The mobile device 100 may be a smartphone, laptop, tablet, or other device able to be used during a fitness routine or exercise session. The mobile device 100 includes a display (e.g., an LCD panel), to present a user interface 104 to the user. The user interface 104 may be used to search for a route upon which the user may run, bike, walk, or otherwise traverse as part of the fitness routine or exercise session. The user may interact with the user interface 104 to provide search parameters, such as a desired duration of the exercise session or a threshold radius of the search (e.g., within five miles of the user's current position). The mobile device 100 may be equipped with various sensors, transducers, radios, and other circuitry to provide geolocation (e.g., GPS), detect acceleration (e.g., an accelerometer or a gyrometer), detect orientation (e.g., a magnetometer), etc. Some of the circuitry may be combined into a single die or integrated circuit, such as with an inertial navigation unit (INU) or an inertial measurement unit (IMU). In addition, the wearable device 102 may include similar devices to detect movement, acceleration, and the like.

To search for a route, the user may initiate the search using the mobile device 100 (e.g., by pressing a user interface control or verbally activating a search mode), then draw a shape in free space. Drawing a shape in free space may be referred to as free-form gesturing or air gesturing in various examples.

Using a path 106 defined by the user's free-form gesture, the mobile device 100 may search for a navigational route that best fits the user's gestured path. In the example shown in FIG. 1, the path 106 is drawn in roughly two dimensions (e.g., on a vertically plane). For the purposes of this discussion, the x-y plane is the vertical plane in front of the user and substantially perpendicular to level ground. The x-y plane may be used in two-dimensional (2D) air gestures. 2D gestures are conventionally drawn in front of the user, as if the user were drawing on a chalkboard. In three-dimensional (3D) air gestures, the z-axis, e.g., the axis that extends out from the user, may be used. Thus, the horizontal plane may be referred to as the x-z plane, and drawing on such a plane would be like drawing on a table top. A 3D air gesture is discussed further in FIG. 2.

In the example illustrated in FIG. 1, the user has drawn an undulating path 106 in substantially the x-y plane. It is understood that some margin for error is allowed as the user may not be able to exactly restrict the air gesture to two dimensions. The beginning of the air gesture 108 may be correlated with the user's current elevation. As the user performs the air gesture to draw the path 106, rises (e.g., upwards movement) in the gesture and resulting path 106 indicate a corresponding rise in elevation and dips in the gesture and resulting path 106 indicate a corresponding fall in elevation. The gesture and resulting path 106 may be drawn from left to right or from right to left, with the beginning of the gesture 108 being correlated with the user's current elevation and also correlated to approximately the current time. The length of the path 106 may be used to indicate a desired distance or time. Whether the length of the path 106 is used to indicate distance or time may be user configurable, such as via the mobile device 100.

Thus, with the input path 106 provided by the user's air gesture in FIG. 1, the mobile device 100 attempts to find a navigational route that includes at least three hills of roughly the elevation increase and decreases indicated by the air gesture, and roughly having a distance that corresponds to the length of the path 106. If the length of the path 106 is configured to indicate a time constraint, then the mobile device 100 may attempt to find a navigational route that roughly matches the desired elevation changes and may be completed in the desired time.

Although FIG. 1 illustrates that the wearable device 102 is used to capture the user's air gesture, it is understood that other mechanisms or devices may be used. For example, the user may wave the mobile device 100 in free space as a gesture. As another example, the user may activate a camera array on the mobile device 100 and gesture in front of the camera array, which may then capture images of the user's arm position throughout the gesture and translate the positions to an air gesture and finally to a path.

In addition, while FIG. 1 illustrates determining a navigational route on the mobile device 100, the present disclosure also encompasses embodiments that modify exercise equipment (e.g., a stationary bicycle, a treadmill, a stair climber, etc.). In such embodiments, instead of determining a navigational route, the configuration of the exercise equipment may be changed. So, for example, instead of attempting to find a route with a steep incline, the user's stationary bicycle may be adjusted to provide more resistance to the spinning wheel (e.g., in the crankcase, flywheel, or braking a freewheel).

Figure 2:
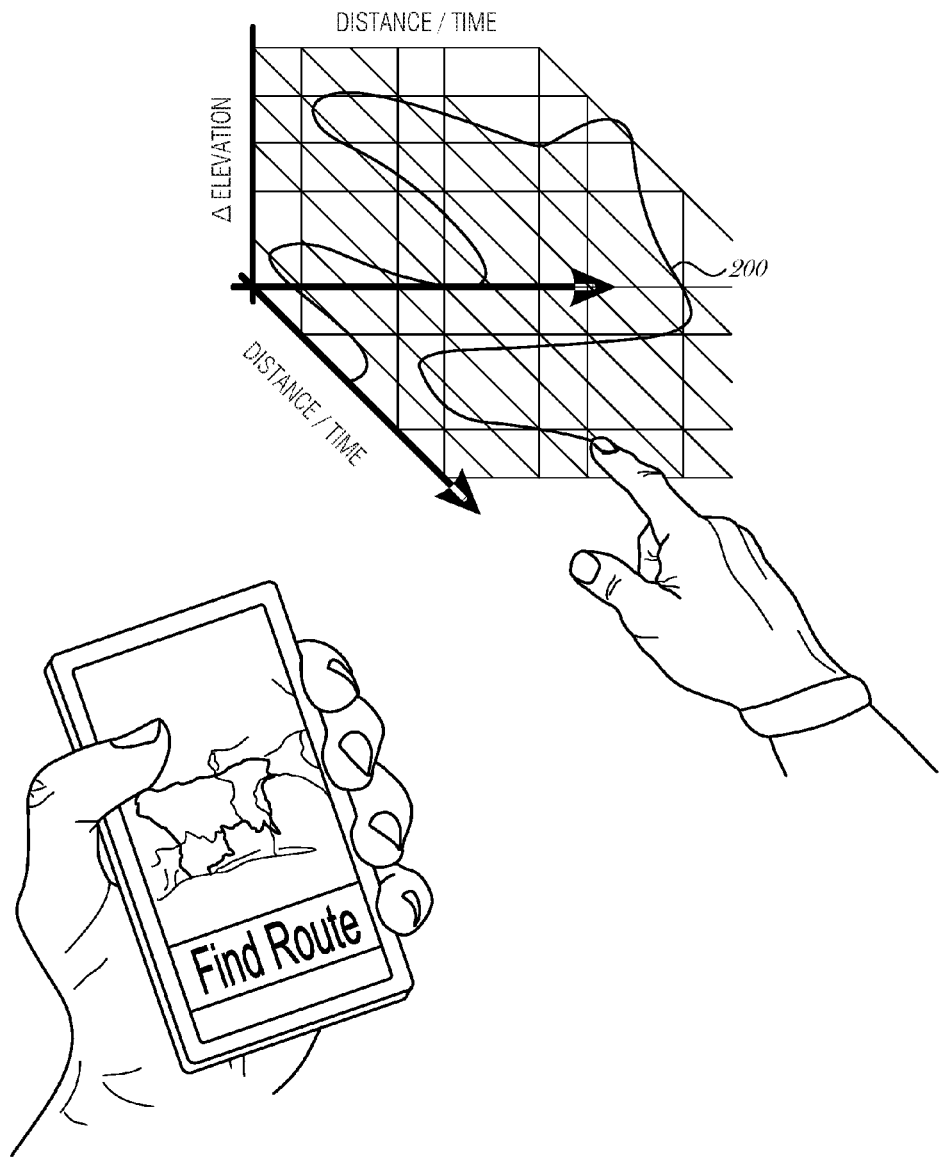
FIG. 2 is a diagram illustrating another example usage, according to an embodiment.

FIG. 2 is a diagram illustrating another example usage, according to an embodiment. As with that in FIG. 1, a user may perform an air gesture to draw a path 200 in free space. In contrast to the path 106 of FIG. 1, the path 200 in FIG. 2 is purposefully drawn in 3D. In the example shown in FIG. 2, the axes for the x-y plane (that vertical to the user and substantially in front of the user) remain the same as that illustrated in FIG. 1 (e.g., x-axis is for distance or time, and y-axis is for elevation changes over distance or time). The addition of the z-axis may be used to provide additional distance or time parameters. With a 3D path 200, the mobile device 100 may search for a navigational route that roughly matches the shape of the path 200. For example, in a simple case, if the user were to draw a flat circular path in the horizontal plane, then the mobile device 100 may search for a roughly circular navigational route with little variation in elevation and with a distance correlating to the length of the drawn path.

In the example illustrated in FIG. 2, the user has drawn a wandering path 200 that includes changes in elevation with an ending point distinctly different from the starting point.

Other aspects of the gesture may be used to indicate features of the desired navigational route or the exercise session. For example, a speed at which the gesture is drawn may be used to indicate a quicker tempo, faster pace, higher resistance, etc. The frequency of a gesture may be used to modify the route or session as well.

Figure 3:
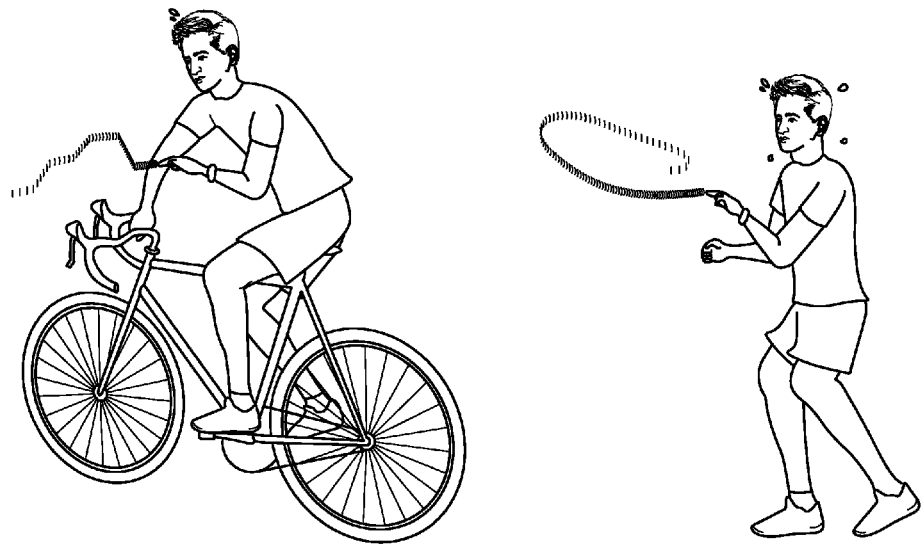
FIG. 3 illustrates examples where the user is moving through the world (e.g., non-stationary) on a bicycle or walking, according to an embodiment.
Figure 4:
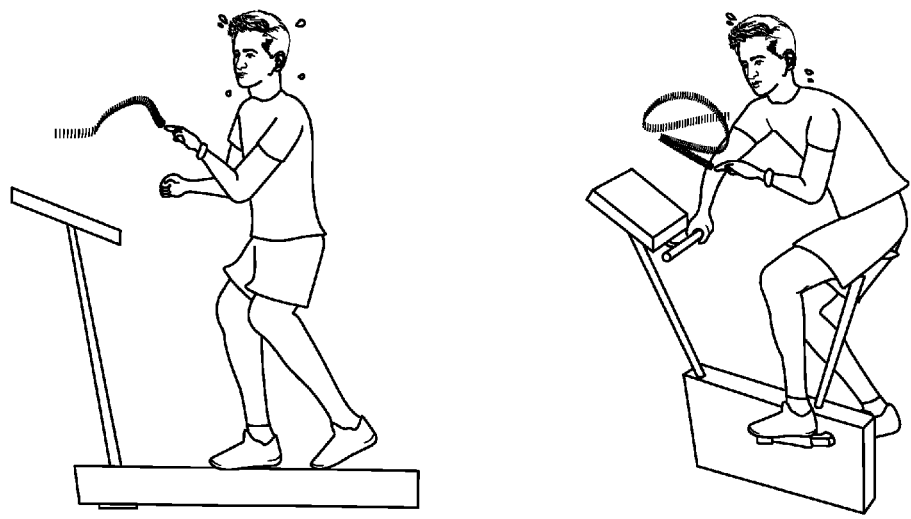
FIG. 4 illustrates examples where the user is not moving through the world (e.g., on a stationary apparatus), according to an embodiment.

FIGS. 3 and 4 illustrate additional examples of usage, according to various embodiments. FIG. 3 illustrates examples where the user is moving through the world (e.g., non-stationary) on a bicycle or walking. In these examples, a second device (e.g., mobile device 100) is not used and instead the search is initiated by the wearable device 102 and results are conveyed to the user via the wearable device 102. For example, the user may initiate a search with a special gesture (e.g., shaking fist, pointing down for a period of time, waving back and forth, etc.), with a verbal command, or with a user interface mechanism on the wearable device 102 (e.g., touchscreen activation or a hard button activation). The special gesture may be configurable so that certain exercises do not inadvertently trigger the special gesture. For example, when bicycling, a punching motion may be used as a special gesture, but when shadow boxing while running is the exercise being performed, a different special gesture may be used.

Alternatively, while not shown, the mobile device 100 may be affixed to or incorporated into the exercise apparatus. For example, in FIG. 3, the mobile device 100 may be affixed to the handle bars of the bicycle. Additionally, a second wearable device may be used as the mobile device 100, for example a smartglasses may be used to provide the visual display to the user, while a smartwatch may be used to capture the air gesture. The smartglasses may be world-facing cameras which may capture the air gesture, in which case, the user may not use a smartwatch. Other configurations are considered to be within the scope of the present disclosure.

FIG. 4 illustrates examples where the user is not moving through the world (e.g., on a stationary apparatus). In such embodiments, the user is not provided a navigational route, but instead is provided a change in the exercise either through the modification of the exercise equipment or by modification of the exercise itself. As an example, the user may provide a 2D air gesture with rises and falls to indicate an increase and decrease, respectively, of the resistance used in a flywheel of a stationary bicycle. The rises and falls of the gesture may be used to control the incline setting on a treadmill, change the resistance on a stair climber, alter the pitch or angle of climbing on a stair climber, change the resistance on a rowing machine, or the like.

As another example, the exercise itself may be modified. For example, the user may be directed to stand up when bicycling, which works different muscles than when seated. Alternatively, the user may be directed to change from running on a treadmill to performing another exercise, such as bicycling to increase or decrease the effect of the workout in accordance with the parameters provided by the user's air gesture. Combinations of such exercise machine modifications and workout alterations may be used as well.

Figure 5:
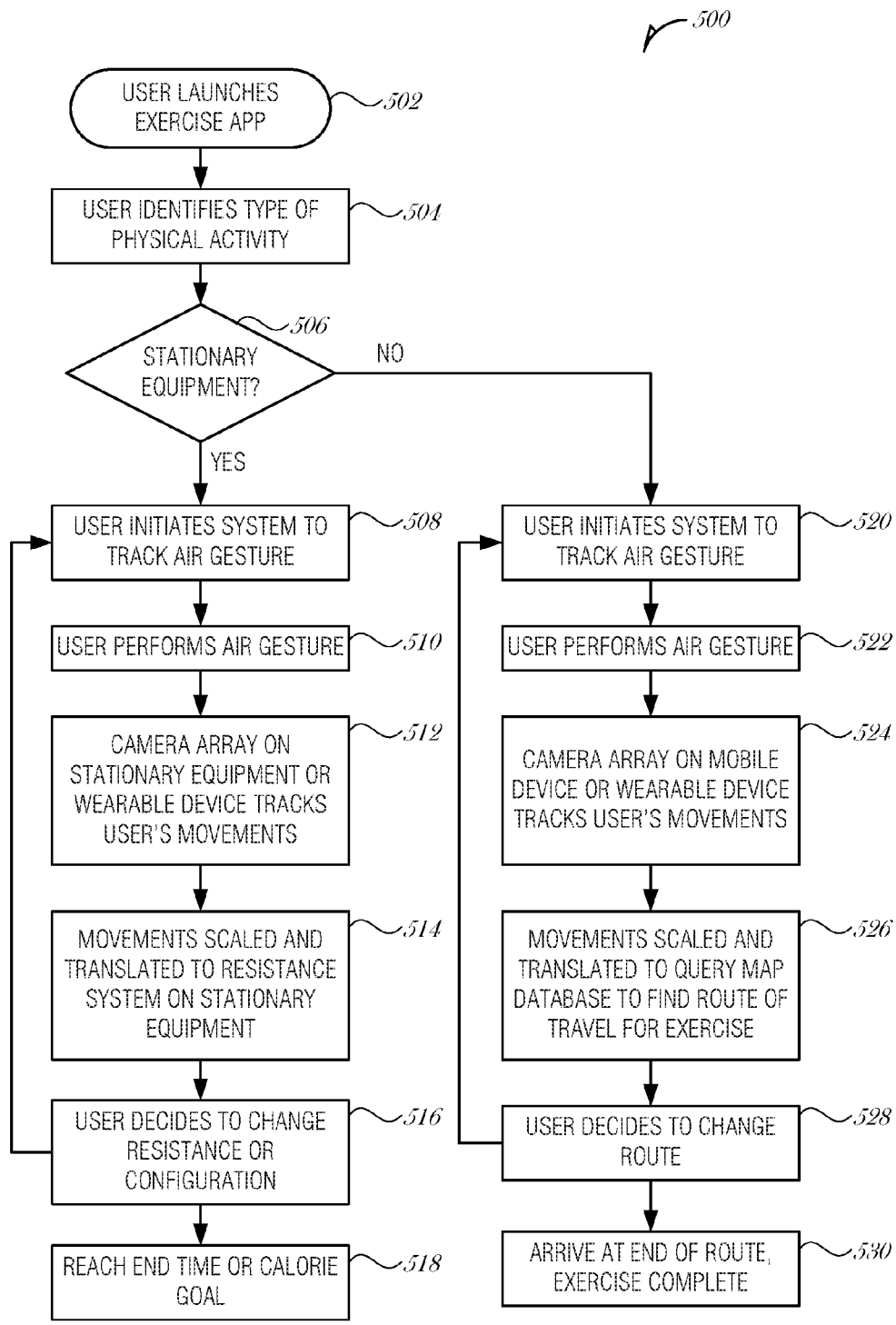
FIG. 5 is a flowchart illustrating a workflow, according an embodiment.

FIG. 5 is a flowchart illustrating a workflow 500, according an embodiment. A user launches an app (operation 502). The app may be executed on a user device (e.g., a smartphone, wearable device, laptop, etc.) or on equipment integrated into or affixed onto exercise equipment. The user identifies a type of physical activity (operation 504). The user may select an activity from various types of user interface controls, such as a dropdown list, radio selection interface, or the like. The app may adapt route selection or resistance controls based on the type of activity selected.

If the activity is an exercise performed on stationary equipment (decision block 506), then the user may initiate an air gesture tracking mode of the app (operation 508). The user may initiate the tracking mode using various mechanisms, such as by activating a user interface control in the app (e.g., a soft button), depressing a hard button the external housing of mobile device or a portion of the exercise apparatus, by using a voice command, by performing a triggering gesture, or the like.

After initiating the gesture tracking mode, the user performs an air gesture (operation 510) and the gesture is captured (operation 512). The gesture may be captured using image analysis, e.g., with a 2D or 3D camera array. The camera array may be incorporated into the exercise apparatus. Alternatively, the gesture may be tracked using one or more wearable devices that the user is wearing. A wrist, arm, hand, finger, or other wearable device may be equipped with IMUs or the like to track the motion of the user's arm, hand, or finger. The gesture is scaled and translated to a 2D path, which is used as a mechanism to control the resistance or configuration of the exercise apparatus (operation 514). For example, a treadmill may be raised or lower to alter an incline that the user is running or walking on. A bicycle may have its freewheel braked so that the user has to exert more effort to pedal.

After some time, the user may desire to change the resistance or configuration of the exercise equipment (stage 516). At this point, the user may then elect to initiate the air gesture tracking mode again (operation 508) and alter the equipment's operation using another air gesture. After the user's workout time expires or a calorie goal is reached, the user's exercise session may complete (stage 518).

If the user initial selects an activity that is not on a stationary exercise equipment, then a slightly different flow is executed. Similar to the stationary exercise case, the user may initiate air gesture tracking (operation 520) and perform an air gesture (operation 522). Using a camera array on a mobile device (e.g., smartglasses or a smartphone), a 2D or 3D representation of the air gesture may be captured (operation 524). Alternatively, a wearable device may be used to track the user's movement by tracking movement through space (e.g., with accelerometers and gyroscopes). The movements may be scaled and translated (e.g., parameterized) for use as an input to a query for a navigational route. The user's mobile device, wearable device, or other device may perform the query locally (e.g., at the mobile device) or may pass the parameterized gesture information and other query parameters to a remote service (e.g., a cloud service) to obtain one or more proposed routes (operation 526). The user may select a route from the proposed routes, after which the user may be navigated over the route (e.g., with verbal directions, a visual map, or the like). After performing some of the exercise routine, or perhaps even before starting one, the user may decide to change the route (state 528), after which the user may initiate gesture tracking again (operation 520) and proceed through the flow. When the user completes the route provided or the exercise is otherwise complete (e.g., the user terminates the routine early), the exercise session is over (stage 530).

Figure 6:
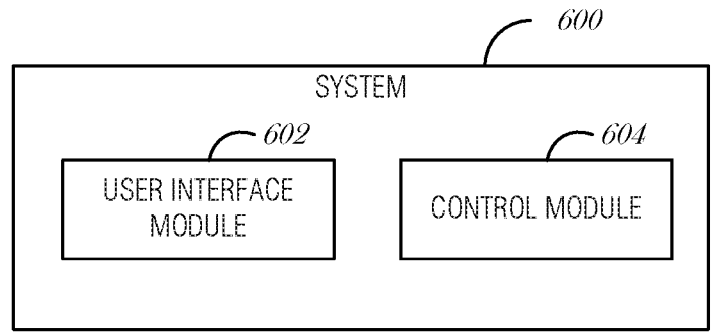
FIG. 6 is a block diagram illustrating system for implementing a health application, according to an embodiment.

FIG. 6 is a block diagram illustrating system 600 for implementing a health application, according to an embodiment. The system 600 may include a user interface module 602 and a control module 604.

The user interface module 602 may be configured to receive, at a user device, a plurality of parameters including a free-form gesture path, the free-form gesture path representing an air gesture performed by a user of the user device. The user device may be any type of mobile compute device including, but not limited to a mobile phone, a smartphone, a phablet, a tablet, a personal digital assistant, a laptop, a digital camera, a wearable device, or the like.

In an embodiment, to receive the plurality of parameters including the free-form gesture path, the user interface module 602 is to receive the free-form gesture path from a wearable device worn by the user and coupled to the user device. The wearable device may be any type of wearable device capable of sensing the motion of the user's body when performing the air gesture, such as a smartring, smartwatch, smartglove, or the like. Thus, in a further embodiment, the wearable device comprises a wrist-based device. In another embodiment, the wearable device comprises a glove-based device. The wearable device may also be one that is equipped with a camera array (e.g., smartglasses). Using the camera array, the wearable device may capture the user's free-form gesture and transmit the gesture to the user interface module 602.

Alternatively, the user may move the user device through free space to perform the gesture. Thus, in an embodiment, to receive the plurality of parameters including the free-form gesture path, the user interface module 602 is to receive the free-form gesture path from the user device.

In an embodiment, to receive the plurality of parameters including the free-form gesture path, the user interface module 602 is to receive the free-form gesture path from a camera system. In a further embodiment, the camera system is incorporated into the user device. In such an embodiment, the user may first initiate capture of the gesture, then perform the gesture in view of a world-facing camera or a user-facing camera. In another embodiment, the camera system is separate from the user device, for example, incorporated into a stationary exercise apparatus.

In an embodiment, the free-form gesture path comprises a path in substantially two-dimensions. In another embodiment, the free-form gesture path comprises a path in three-dimensions. The user may configure the type of path to capture using the user interface module 602, such as with a menu system or a user interface command Other parameters may be provided to the user interface module 602 from the user, such as a calorie target, a preferred type of route, a duration for the workout, a preferred mode of travel, and the like. Such parameters may be used in conjunction with the free-form gesture to determine a route or control exercise apparatus.

Thus, using the plurality of parameters and at least the free-form gesture provided by the user, the control module 604 may be configured to adjust a fitness routine of the user based on the plurality of parameters.

In an embodiment, to adjust the fitness routine for the user, the control module 604 is to adjusting at least one of: a resistance or an incline setting of an exercise apparatus used in the fitness routine. Resistance settings are useful for certain types of exercise apparatus, such as bicycles or rowing machines. Incline settings are useful for a treadmill, stair climber, or skating treadmill.

In an embodiment, to adjust the fitness routine for the user, the control module control module 604 is to analyze the free-form gesture path to obtain a path morphology, use the path morphology to determine a navigation route, and present the navigation route to the user. The path morphology may be parameterized as one or more functions in an x-y coordinate system. The functions may be used with a morphology matching algorithm that analyzes geographical and topographical data from a geographic information system (GIS), for example, to determine a route that best fits the path morphology. The path morphology may be segmented into one or more portions, and the portions may be used to search the GIS database for a route. For example, if the user gestures a form that has several rises and falls, the best route that fits may be a route that repeats a certain number of times. So the user may be provided a route that repeats several times, or a route that has a section that repeats, as the route that best fits the user's gesture input.

In an embodiment, to analyze the free-form gesture path, the control module 604 is to parameterize the free-form gesture path into a coordinate system to produce a parameterized free-form path. In such an embodiment, to use the path morphology to determine the navigation route, the control module 604 is to transmit the parameterized free-form path to a remote server to obtain the navigation route. The remote server may be a GIS server, map server, cloud server, navigation server, or other cloud service that is able to search topographical and geographical maps to determine routes that may match the user's gesture input. The user's current location may be provided to such a server in order to narrow the search space. The user may also provide a maximum search radius (e.g., five miles) to limit the amount of travel needed before beginning a workout. The user's current location may be obtained from the user device or a wearable device operated or worn by the user, e.g., with GPS.

A short gesture may be interpreted as a short workout or a short route. A longer gesture may be interpreted as the user desiring a longer workout or longer route. Thus, in an embodiment, to analyze the free-form gesture path, the control module 604 is to parameterize the free-form gesture path into a coordinate system to produce a parameterized free-form path. In such an embodiment, to use the path morphology to determine the navigation route, the control module 604 is to fit the parameterized free-form path to a route with similar geographical topology. In a further embodiment, to parameterize the free-form gesture path into the coordinate system to produce a parameterized free-form path, the control module 604 is to use the length of the free-form path to parameterize a duration of an exercise session.

In another embodiment, to parameterize the free-form gesture path into the coordinate system to produce a parameterized free-form path, the control module 604 is to use the shape of the free-form path in the x-z plane to parameterize a shape of the navigational route. The shape may indicate that the user desires to run in roughly a circular route, ending near their starting position. As such, the control module 604 may constrain the map search to search for routes that end approximately where they begin. Other shapes may be used in the route search, such as when a user gestures a triangle, routes with roughly three substantially straight courses may be searched. If there is In another embodiment, to parameterize the free-form gesture path into the coordinate system to produce a parameterized free-form path, the control module 604 is to use the shape of the free-form path in the x-y plane to parameterize an intensity over time of an exercise session. In a further embodiment, to use the shape of the free-form path in the x-y plane to parameterize the intensity over time of an exercise session, the control module 604 is to use a frequency or intensity of movement in the free-form path to parameterize the intensity over time.

In an embodiment, the plurality of parameters include a target duration of an exercise session of the fitness routine, and to use the path morphology to determine the navigation route, the control module 604 is to modify the navigation route to fit the target duration. The user may input the target duration on the user device, for example with a drop down menu or a text input box. The duration may affect the distance of the route, depending on the mode of travel.

In an embodiment, the plurality of parameters include a target calorie expenditure during an exercise session of the fitness routine, and to use the path morphology to determine the navigation route, the control module 604 is to modify the navigation route to fit the target calorie expenditure. Similar to distance, the user may provide a target calorie deficit for a workout. The calorie and distance may be provided together. Calorie expenditure may be estimated based on the user's weight, mode of travel, distance, elevation change, and the like.

In an embodiment, to use the path morphology to determine the navigation route, the control module 604 is to obtain a proposed route based on the path morphology, analyze vehicle traffic patterns of the proposed route, and select the proposed route as the navigation route when the vehicle traffic patterns are less than a threshold activity level. Vehicle patterns may be obtained from a traffic monitoring service, such as a department of motor vehicles (DMV) service. When running or biking, heavy traffic may be more dangerous. As such, the proposed route may be one with less overall traffic, fewer intersections to cross, or incorporate pedestrian bridges and the like into the route, for example.

Figure 7:
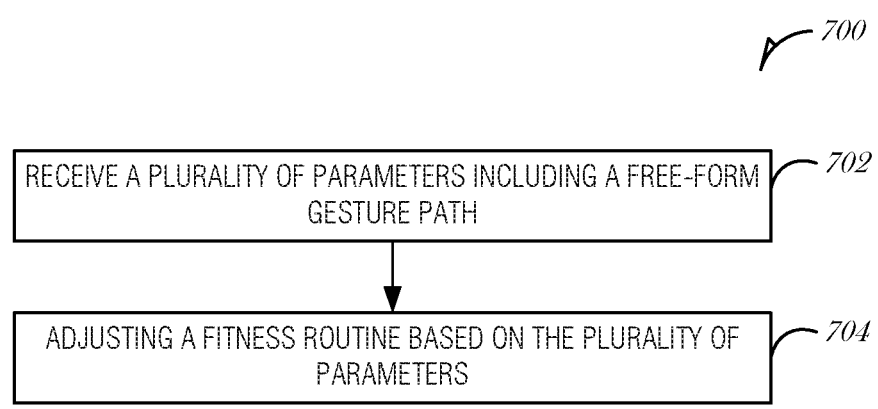
FIG. 7 is a flowchart illustrating a method of implementing a health application, according to an embodiment.

FIG. 7 is a flowchart illustrating a method 700 of implementing a health application, according to an embodiment. At block 702, a plurality of parameters including a free-form gesture path is received at a user device, where the free-form gesture path representing an air gesture performed by a user of the user device.

At block 704, a fitness routine of the user is adjusted based on the plurality of parameters.

In an embodiment, receiving the plurality of parameters including the free-form gesture path comprises receiving the free-form gesture path from a wearable device worn by the user and coupled to the user device. In an embodiment, the wearable device comprises a wrist-based device. In another embodiment, the wearable device comprises a glove-based device.

In an embodiment, receiving the plurality of parameters including the free-form gesture path comprises receiving the free-form gesture path from the user device.

In an embodiment, receiving the plurality of parameters including the free-form gesture path comprises receiving the free-form gesture path from a camera system. In a further embodiment, the camera system is incorporated into the user device. In another embodiment, the camera system is separate from the user device.

In an embodiment, the free-form gesture path comprises a path in substantially two-dimensions. In another embodiment, the free-form gesture path comprises a path in three-dimensions.

In an embodiment, adjusting the fitness routine for the user comprises adjusting at least one of: a resistance or an incline setting of an exercise apparatus used in the fitness routine.

In an embodiment, adjusting the fitness routine for the user comprises analyzing the free-form gesture path to obtain a path morphology, using the path morphology to determine a navigation route, and presenting the navigation route to the user. In a further embodiment, analyzing the free-form gesture path comprises parameterizing the free-form gesture path into a coordinate system to produce a parameterized free-form path. In such an embodiment, using the path morphology to determine the navigation route comprises transmitting the parameterized free-form path to a remote server to obtain the navigation route.

In an embodiment, analyzing the free-form gesture path comprises parameterizing the free-form gesture path into a coordinate system to produce a parameterized free-form path. In such an embodiment, using the path morphology to determine the navigation route comprises fitting the parameterized free-form path to a route with similar geographical topology.

In a further embodiment, parameterizing the free-form gesture path into the coordinate system to produce a parameterized free-form path comprises using the length of the free-form path to parameterize a duration of an exercise session. In another embodiment, parameterizing the free-form gesture path into the coordinate system to produce a parameterized free-form path comprises using the shape of the free-form path in the x-z plane to parameterize a shape of the navigational route. In another embodiment, parameterizing the free-form gesture path into the coordinate system to produce a parameterized free-form path comprises using the shape of the free-form path in the x-y plane to parameterize an intensity over time of an exercise session. In a further embodiment, using the shape of the free-form path in the x-y plane to parameterize the intensity over time of an exercise session comprises using a frequency or intensity of movement in the free-form path to parameterize the intensity over time.

In an embodiment, the plurality of parameters include a target duration of an exercise session of the fitness routine, and wherein using the path morphology to determine the navigation route comprises modifying the navigation route to fit the target duration.

In an embodiment, the plurality of parameters include a target calorie expenditure during an exercise session of the fitness routine, and wherein using the path morphology to determine the navigation route comprises modifying the navigation route to fit the target calorie expenditure.

In an embodiment, using the path morphology to determine the navigation route comprises obtaining a proposed route based on the path morphology, analyzing vehicle traffic patterns of the proposed route, and selecting the proposed route as the navigation route when the vehicle traffic patterns are less than a threshold activity level.

In an embodiment, the other parameters or further indications may be provided with other input modalities, such as audio input. Other novel input mechanisms may be utilized as well, for example touching the back of the device with changing pressure while performing the gesture may indicate varying difficulty or desired elevation for the route being drawn.

Embodiments may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

A processor subsystem may be used to execute the instruction on the machine-readable medium. The processor subsystem may include one or more processors, each with one or more cores. Additionally, the processor subsystem may be disposed on one or more physical devices. The processor subsystem may include one or more specialized processors, such as a graphics processing unit (GPU), a digital signal processor (DSP), a field programmable gate array (FPGA), or a fixed function processor.

Examples, as described herein, may include, or may operate on, logic or a number of components, modules, or mechanisms. Modules may be hardware, software, or firmware communicatively coupled to one or more processors in order to carry out the operations described herein. Modules may be hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 8:
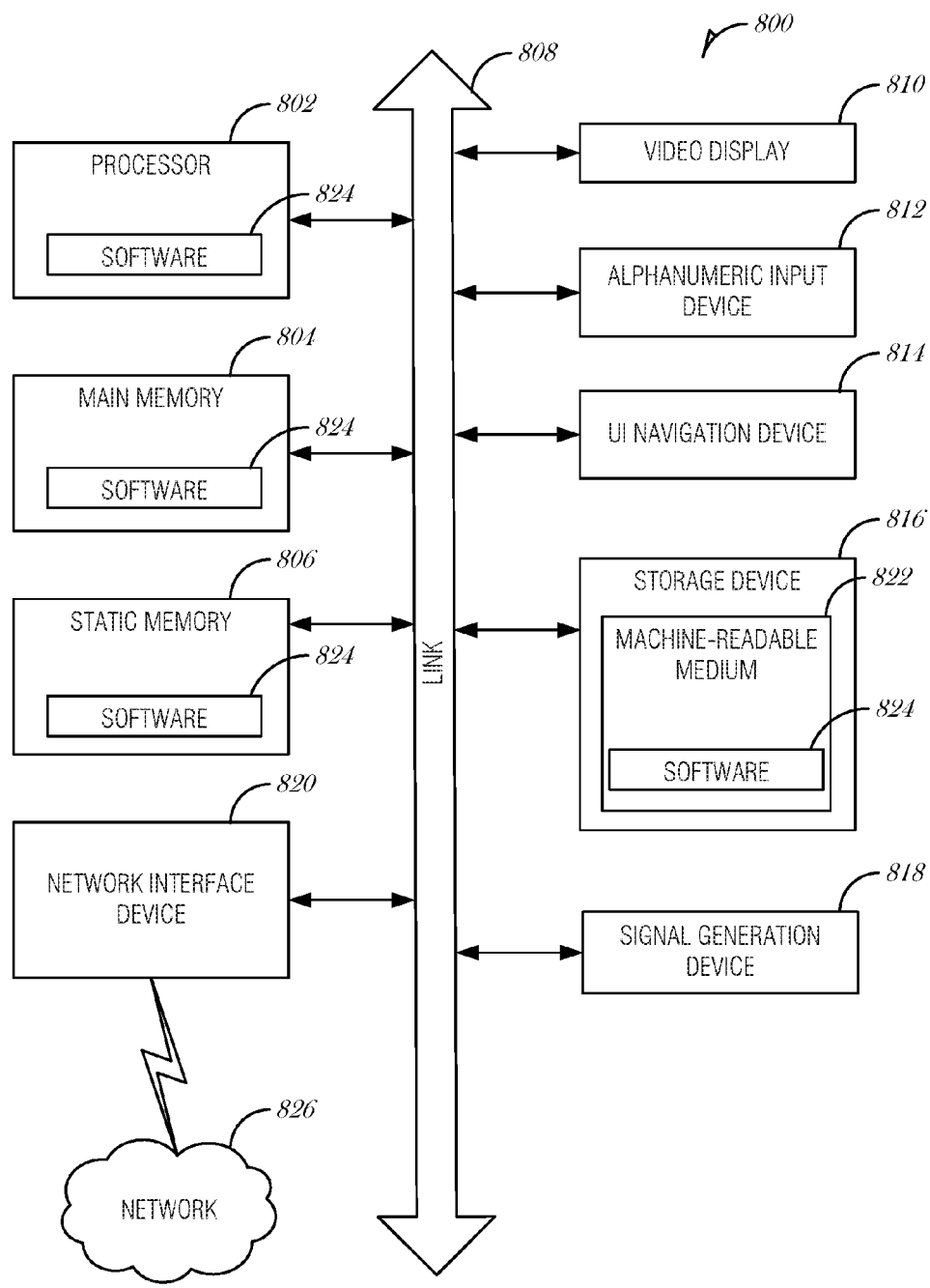
FIG. 8 is a block diagram illustrating an example machine upon which any one or more of the techniques (e.g., methodologies) discussed herein may perform, according to an example embodiment.

FIG. 8 is a block diagram illustrating a machine in the example form of a computer system 800, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be an onboard vehicle system, wearable device, personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 800 includes at least one processor 802 (e.g., a central processing unit (CPU), a graphics processing unit (GPU) or both, processor cores, compute nodes, etc.), a main memory 804 and a static memory 806, which communicate with each other via a link 808 (e.g., bus). The computer system 800 may further include a video display unit 810, an alphanumeric input device 812 (e.g., a keyboard), and a user interface (UI) navigation device 814 (e.g., a mouse). In one embodiment, the video display unit 810, input device 812 and UI navigation device 814 are incorporated into a touch screen display. The computer system 800 may additionally include a storage device 816 (e.g., a drive unit), a signal generation device 818 (e.g., a speaker), a network interface device 820, and one or more sensors (not shown), such as a global positioning system (GPS) sensor, compass, accelerometer, gyrometer, magnetometer, or other sensor.

The storage device 816 includes a machine-readable medium 822 on which is stored one or more sets of data structures and instructions 824 (e.g., software) embodying or utilized by any one or more of the methodologies or functions described herein. The instructions 824 may also reside, completely or at least partially, within the main memory 804, static memory 806, and/or within the processor 802 during execution thereof by the computer system 800, with the main memory 804, static memory 806, and the processor 802 also constituting machine-readable media.

While the machine-readable medium 822 is illustrated in an example embodiment to be a single medium, the term "machine-readable medium" may include a single medium or multiple media (e.g., a centralized or distributed database, and/or associated caches and servers) that store the one or more instructions 824. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Bluetooth/BLE, Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

ADDITIONAL NOTES & EXAMPLES

Example 1 includes subject matter (such as a device, apparatus, or machine) for implementing a health application comprising: a user interface module to receive, at a user device, a plurality of parameters including a free-form gesture path, the free-form gesture path representing an air gesture performed by a user of the user device; and a control module to adjust a fitness routine of the user based on the plurality of parameters.

In Example 2, the subject matter of Example 1 may include, wherein to receive the plurality of parameters the free-form gesture path, the user interface module is to receive the free-form gesture path from a wearable device worn by the user and coupled to the user device.

In Example 3, the subject matter of any one of Examples 1 to 2 may include, wherein the wearable device comprises a wrist-based device.

In Example 4, the subject matter of any one of Examples 1 to 3 may include, wherein the wearable device comprises a glove-based device.

In Example 5, the subject matter of any one of Examples 1 to 4 may include, wherein to receive the plurality of parameters the free-form gesture path, the user interface module is to receive the free-form gesture path from the user device.

In Example 6, the subject matter of any one of Examples 1 to 5 may include, wherein to receive the plurality of parameters the free-form gesture path, the user interface module is to receive the free-form gesture path from a camera system.

In Example 7, the subject matter of any one of Examples 1 to 6 may include, wherein the camera system is incorporated into the user device.

In Example 8, the subject matter of any one of Examples 1 to 7 may include, wherein the camera system is separate from the user device.

In Example 9, the subject matter of any one of Examples 1 to 8 may include, wherein the free-form gesture path comprises a path in substantially two-dimensions.

In Example 10, the subject matter of any one of Examples 1 to 9 may include, wherein the free-form gesture path comprises a path in three-dimensions.

In Example 11, the subject matter of any one of Examples 1 to 10 may include, wherein to adjust the fitness routine for the user, the control module is to adjust at least one of: a resistance or an incline setting of an exercise apparatus used in the fitness routine.

In Example 12, the subject matter of any one of Examples 1 to 11 may include, wherein to adjust the fitness routine for the user, the control module is to: analyze the free-form gesture path to obtain a path morphology; use the path morphology to determine a navigation route; and present the navigation route to the user.

In Example 13, the subject matter of any one of Examples 1 to 12 may include, wherein to analyze the free-form gesture path, the control module is to parameterize the free-form gesture path into a coordinate system to produce a parameterized free-form path; and wherein to use the path morphology to determine the navigation route, the control module is to transmit the parameterized free-form path to a remote server to obtain the navigation route.

In Example 14, the subject matter of any one of Examples 1 to 13 may include, wherein to analyze the free-form gesture path, the control module is to parameterize the free-form gesture path into a coordinate system to produce a parameterized free-form path; and wherein to use the path morphology to determine the navigation route, the control module is to fit the parameterized free-form path to a route with similar geographical topology.

In Example 15, the subject matter of any one of Examples 1 to 14 may include, wherein to parameterize the free-form gesture path into the coordinate system to produce a parameterized free-form path, the control module is to use the length of the free-form path to parameterize a duration of an exercise session.

In Example 16, the subject matter of any one of Examples 1 to 15 may include, wherein to parameterize the free-form gesture path into the coordinate system to produce a parameterized free-form path, the control module is to use the shape of the free-form path in the x-z plane to parameterize a shape of the navigational route.

In Example 17, the subject matter of any one of Examples 1 to 16 may include, wherein to parameterize the free-form gesture path into the coordinate system to produce a parameterized free-form path, the control module is to use the shape of the free-form path in the x-y plane to parameterize an intensity over time of an exercise session.

In Example 18, the subject matter of any one of Examples 1 to 17 may include, wherein to use the shape of the free-form path in the x-y plane to parameterize the intensity over time of an exercise session, the control module is to use a frequency or intensity of movement in the free-form path to parameterize the intensity over time.

In Example 19, the subject matter of any one of Examples 1 to 18 may include, wherein the plurality of parameters include a target duration of an exercise session of the fitness routine, and wherein to use the path morphology to determine the navigation route, the control module is to modify the navigation route to fit the target duration.

In Example 20, the subject matter of any one of Examples 1 to 19 may include, wherein the plurality of parameters include a target calorie expenditure during an exercise session of the fitness routine, and wherein to use the path morphology to determine the navigation route, the control module is to modify the navigation route to fit the target calorie expenditure.

In Example 21, the subject matter of any one of Examples 1 to 20 may include, wherein to use the path morphology to determine the navigation route, the control module is to: obtain a proposed route based on the path morphology; analyze vehicle traffic patterns of the proposed route; and select the proposed route as the navigation route when the vehicle traffic patterns are less than a threshold activity level.

Example 22 includes subject matter (such as a method, means for performing acts, machine readable medium including instructions that when performed by a machine cause the machine to performs acts, or an apparatus to perform) for implementing a health application comprising: receiving, at a user device, a plurality of parameters including a free-form gesture path, the free-form gesture path representing an air gesture performed by a user of the user device; and adjusting a fitness routine of the user based on the plurality of parameters.

In Example 23, the subject matter of Example 22 may include, wherein receiving the plurality of parameters the free-form gesture path comprises receiving the free-form gesture path from a wearable device worn by the user and coupled to the user device.

In Example 24, the subject matter of any one of Examples 22 to 23 may include, wherein the wearable device comprises a wrist-based device.

In Example 25, the subject matter of any one of Examples 22 to 24 may include, wherein the wearable device comprises a glove-based device.

In Example 26, the subject matter of any one of Examples 22 to 25 may include, wherein receiving the plurality of parameters the free-form gesture path comprises receiving the free-form gesture path from the user device.

In Example 27, the subject matter of any one of Examples 22 to 26 may include, wherein receiving the plurality of parameters the free-form gesture path comprises receiving the free-form gesture path from a camera system.

In Example 28, the subject matter of any one of Examples 22 to 27 may include, wherein the camera system is incorporated into the user device.

In Example 29, the subject matter of any one of Examples 22 to 28 may include, wherein the camera system is separate from the user device.

In Example 30, the subject matter of any one of Examples 22 to 29 may include, wherein the free-form gesture path comprises a path in substantially two-dimensions.

In Example 31, the subject matter of any one of Examples 22 to 30 may include, wherein the free-form gesture path comprises a path in three-dimensions.

In Example 32, the subject matter of any one of Examples 22 to 31 may include, wherein adjusting the fitness routine for the user comprises adjusting at least one of: a resistance or an incline setting of an exercise apparatus used in the fitness routine.

In Example 33, the subject matter of any one of Examples 22 to 32 may include, wherein adjusting the fitness routine for the user comprises: analyzing the free-form gesture path to obtain a path morphology; using the path morphology to determine a navigation route; and presenting the navigation route to the user.

In Example 34, the subject matter of any one of Examples 22 to 33 may include, wherein analyzing the free-form gesture path comprises parameterizing the free-form gesture path into a coordinate system to produce a parameterized free-form path; and wherein using the path morphology to determine the navigation route comprises transmitting the parameterized free-form path to a remote server to obtain the navigation route.

In Example 35, the subject matter of any one of Examples 22 to 34 may include, wherein analyzing the free-form gesture path comprises parameterizing the free-form gesture path into a coordinate system to produce a parameterized free-form path; and wherein using the path morphology to determine the navigation route comprises fitting the parameterized free-form path to a route with similar geographical topology.

In Example 36, the subject matter of any one of Examples 22 to 35 may include, wherein parameterizing the free-form gesture path into the coordinate system to produce a parameterized free-form path comprises using the length of the free-form path to parameterize a duration of an exercise session.

In Example 37, the subject matter of any one of Examples 22 to 36 may include, wherein parameterizing the free-form gesture path into the coordinate system to produce a parameterized free-form path comprises using the shape of the free-form path in the x-z plane to parameterize a shape of the navigational route.

In Example 38, the subject matter of any one of Examples 22 to 37 may include, wherein parameterizing the free-form gesture path into the coordinate system to produce a parameterized free-form path comprises using the shape of the free-form path in the x-y plane to parameterize an intensity over time of an exercise session.

In Example 39, the subject matter of any one of Examples 22 to 38 may include, wherein using the shape of the free-form path in the x-y plane to parameterize the intensity over time of an exercise session comprises using a frequency or intensity of movement in the free-form path to parameterize the intensity over time.

In Example 40, the subject matter of any one of Examples 22 to 39 may include, wherein the plurality of parameters include a target duration of an exercise session of the fitness routine, and wherein using the path morphology to determine the navigation route comprises modifying the navigation route to fit the target duration.

In Example 41, the subject matter of any one of Examples 22 to 40 may include, wherein the plurality of parameters include a target calorie expenditure during an exercise session of the fitness routine, and wherein using the path morphology to determine the navigation route comprises modifying the navigation route to fit the target calorie expenditure.

In Example 42, the subject matter of any one of Examples 22 to 41 may include, wherein using the path morphology to determine the navigation route comprises: obtaining a proposed route based on the path morphology; analyzing vehicle traffic patterns of the proposed route; and selecting the proposed route as the navigation route when the vehicle traffic patterns are less than a threshold activity level.

Example 43 includes at least one machine-readable medium including instructions, which when executed by a machine, cause the machine to perform operations of any of the Examples 22-42.

Example 44 includes an apparatus comprising means for performing any of the Examples 22-42.

Example 45 includes subject matter (such as a device, apparatus, or machine) for implementing a health application comprising: means for receiving, at a user device, a plurality of parameters including a free-form gesture path, the free-form gesture path representing an air gesture performed by a user of the user device; and means for adjusting a fitness routine of the user based on the plurality of parameters.

In Example 46, the subject matter of Example 45 may include, wherein the means for receiving the plurality of parameters the free-form gesture path comprise means for receiving the free-form gesture path from a wearable device worn by the user and coupled to the user device.

In Example 47, the subject matter of any one of Examples 45 to 46 may include, wherein the wearable device comprises a wrist-based device.

In Example 48, the subject matter of any one of Examples 45 to 47 may include, wherein the wearable device comprises a glove-based device.

In Example 49, the subject matter of any one of Examples 45 to 48 may include, wherein the means for receiving the plurality of parameters the free-form gesture path comprise means for receiving the free-form gesture path from the user device.

In Example 50, the subject matter of any one of Examples 45 to 49 may include, wherein the means for receiving the plurality of parameters the free-form gesture path comprise means for receiving the free-form gesture path from a camera system.

In Example 51, the subject matter of any one of Examples 45 to 50 may include, wherein the camera system is incorporated into the user device.

In Example 52, the subject matter of any one of Examples 45 to 51 may include, wherein the camera system is separate from the user device.

In Example 53, the subject matter of any one of Examples 45 to 52 may include, wherein the free-form gesture path comprises a path in substantially two-dimensions.

In Example 54, the subject matter of any one of Examples 45 to 53 may include, wherein the free-form gesture path comprises a path in three-dimensions.

In Example 55, the subject matter of any one of Examples 45 to 54 may include, wherein the means for adjusting the fitness routine for the user comprise means for adjusting at least one of: a resistance or an incline setting of an exercise apparatus used in the fitness routine.

In Example 56, the subject matter of any one of Examples 45 to 55 may include, wherein the means for adjusting the fitness routine for the user comprise: means for analyzing the free-form gesture path to obtain a path morphology; means for using the path morphology to determine a navigation route; and means for presenting the navigation route to the user.

In Example 57, the subject matter of any one of Examples 45 to 56 may include, wherein the means for analyzing the free-form gesture path comprise means for parameterizing the free-form gesture path into a coordinate system to produce a parameterized free-form path; and wherein the means for using the path morphology to determine the navigation route comprise means for transmitting the parameterized free-form path to a remote server to obtain the navigation route.

In Example 58, the subject matter of any one of Examples 45 to 57 may include, wherein the means for analyzing the free-form gesture path comprise means for parameterizing the free-form gesture path into a coordinate system to produce a parameterized free-form path; and wherein the means for using the path morphology to determine the navigation route comprise means for fitting the parameterized free-form path to a route with similar geographical topology.

In Example 59, the subject matter of any one of Examples 45 to 58 may include, wherein the means for parameterizing the free-form gesture path into the coordinate system to produce a parameterized free-form path comprise means for using the length of the free-form path to parameterize a duration of an exercise session.

In Example 60, the subject matter of any one of Examples 45 to 59 may include, wherein the means for parameterizing the free-form gesture path into the coordinate system to produce a parameterized free-form path comprise means for using the shape of the free-form path in the x-z plane to parameterize a shape of the navigational route.

In Example 61, the subject matter of any one of Examples 45 to 60 may include, wherein the means for parameterizing the free-form gesture path into the coordinate system to produce a parameterized free-form path comprise means for using the shape of the free-form path in the x-y plane to parameterize an intensity over time of an exercise session.

In Example 62, the subject matter of any one of Examples 45 to 61 may include, wherein the means for using the shape of the free-form path in the x-y plane to parameterize the intensity over time of an exercise session comprise means for using a frequency or intensity of movement in the free-form path to parameterize the intensity over time.

In Example 63, the subject matter of any one of Examples 45 to 62 may include, wherein the plurality of parameters include a target duration of an exercise session of the fitness routine, and wherein the means for using the path morphology to determine the navigation route comprise means for modifying the navigation route to fit the target duration.

In Example 64, the subject matter of any one of Examples 45 to 63 may include, wherein the plurality of parameters include a target calorie expenditure during an exercise session of the fitness routine, and wherein the means for using the path morphology to determine the navigation route comprise means for modifying the navigation route to fit the target calorie expenditure.

In Example 65, the subject matter of any one of Examples 45 to 64 may include, wherein the means for using the path morphology to determine the navigation route comprises: means for obtaining a proposed route based on the path morphology; means for analyzing vehicle traffic patterns of the proposed route; and means for selecting the proposed route as the navigation route when the vehicle traffic patterns are less than a threshold activity level.

Example 66 includes subject matter (such as a device, apparatus, or machine) for implementing a health application comprising: a processor subsystem; and a memory including instructions, which when executed by the processor subsystem, cause the processor subsystem to: receive, at a user device, a plurality of parameters including a free-form gesture path, the free-form gesture path representing an air gesture performed by a user of the user device; and adjust a fitness routine of the user based on the plurality of parameters.

In Example 67, the subject matter of Example 66 may include, wherein the instructions to receive the plurality of parameters the free-form gesture path comprise instructions to receive the free-form gesture path from a wearable device worn by the user and coupled to the user device.

In Example 68, the subject matter of any one of Examples 66 to 67 may include, wherein the wearable device comprises a wrist-based device.

In Example 69, the subject matter of any one of Examples 66 to 68 may include, wherein the wearable device comprises a glove-based device.

In Example 70, the subject matter of any one of Examples 66 to 69 may include, wherein the instructions to receive the plurality of parameters the free-form gesture path comprise instructions to receive the free-form gesture path from the user device.

In Example 71, the subject matter of any one of Examples 66 to 70 may include, wherein the instructions to receive the plurality of parameters the free-form gesture path comprise instructions to receive the free-form gesture path from a camera system.

In Example 72, the subject matter of any one of Examples 66 to 71 may include, wherein the camera system is incorporated into the user device.

In Example 73, the subject matter of any one of Examples 66 to 72 may include, wherein the camera system is separate from the user device.

In Example 74, the subject matter of any one of Examples 66 to 73 may include, wherein the free-form gesture path comprises a path in substantially two-dimensions.

In Example 75, the subject matter of any one of Examples 66 to 74 may include, wherein the free-form gesture path comprises a path in three-dimensions.

In Example 76, the subject matter of any one of Examples 66 to 75 may include, wherein the instructions to adjust the fitness routine for the user comprise instructions to adjust at least one of: a resistance or an incline setting of an exercise apparatus used in the fitness routine.

In Example 77, the subject matter of any one of Examples 66 to 76 may include, wherein the instructions to adjust the fitness routine for the user comprise instructions to: analyze the free-form gesture path to obtain a path morphology; use the path morphology to determine a navigation route; and present the navigation route to the user.

In Example 78, the subject matter of any one of Examples 66 to 77 may include, wherein the instructions to analyze the free-form gesture path comprise instructions to parameterize the free-form gesture path into a coordinate system to produce a parameterized free-form path; and wherein the instructions to use the path morphology to determine the navigation route comprise instructions to transmit the parameterized free-form path to a remote server to obtain the navigation route.

In Example 79, the subject matter of any one of Examples 66 to 78 may include, wherein the instructions to analyze the free-form gesture path comprise instructions to parameterize the free-form gesture path into a coordinate system to produce a parameterized free-form path; and wherein the instructions to use the path morphology to determine the navigation route comprise instructions to fit the parameterized free-form path to a route with similar geographical topology.

In Example 80, the subject matter of any one of Examples 66 to 79 may include, wherein the instructions to parameterize the free-form gesture path into the coordinate system to produce a parameterized free-form path comprise instructions to use the length of the free-form path to parameterize a duration of an exercise session.

In Example 81, the subject matter of any one of Examples 66 to 80 may include, wherein the instructions to parameterize the free-form gesture path into the coordinate system to produce a parameterized free-form path comprise instructions to use the shape of the free-form path in the x-z plane to parameterize a shape of the navigational route.

In Example 82, the subject matter of any one of Examples 66 to 81 may include, wherein the instructions to parameterize the free-form gesture path into the coordinate system to produce a parameterized free-form path comprise instructions to use the shape of the free-form path in the x-y plane to parameterize an intensity over time of an exercise session.

In Example 83, the subject matter of any one of Examples 66 to 82 may include, wherein the instructions to use the shape of the free-form path in the x-y plane to parameterize the intensity over time of an exercise session comprise instructions to use a frequency or intensity of movement in the free-form path to parameterize the intensity over time.

In Example 84, the subject matter of any one of Examples 66 to 83 may include, wherein the plurality of parameters include a target duration of an exercise session of the fitness routine, and wherein the instructions to use the path morphology to determine the navigation route comprise instructions to modify the navigation route to fit the target duration.

In Example 85, the subject matter of any one of Examples 66 to 84 may include, wherein the plurality of parameters include a target calorie expenditure during an exercise session of the fitness routine, and wherein the instructions to use the path morphology to determine the navigation route comprise instructions to modify the navigation route to fit the target calorie expenditure.

In Example 86, the subject matter of any one of Examples 66 to 85 may include, wherein the instructions to use the path morphology to determine the navigation route comprise instructions to: obtain a proposed route based on the path morphology; analyze vehicle traffic patterns of the proposed route; and select the proposed route as the navigation route when the vehicle traffic patterns are less than a threshold activity level.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A system for implementing a health application, the system comprising:

a user interface module to receive, at a user device, a plurality of parameters including a free-form gesture path, the free-form gesture path representing an air gesture performed by a user of the user device; and a control module to adjust a fitness routine of the user based on the plurality of parameters, wherein to adjust the fitness routine for the user the control module is to:

analyze the free-form gesture path to obtain a path morphology, parameterize the free-form gesture path into a coordinate system to produce a parameterized free-form path, and use the shape of the free-form path in the x-y plane to parameterize an intensity over time of an exercise session;

use the path morphology to determine a navigation route and fit the parameterized free-form path to a route with similar geographical topology; and present the navigation route to the user.

2. The system of claim 1, wherein to receive the plurality of parameters including the free-form gesture path, the user interface module is to receive the free-form gesture path from a wearable device worn by the user and coupled to the user device.

3. The system of claim 2, wherein the wearable device comprises a wrist-based device.

4. The system of claim 2, wherein the wearable device comprises a glove-based device.

5. The system of claim 1, wherein to receive the plurality of parameters including the free-form gesture path, the user interface module is to receive the free-form gesture path from the user device.

6. The system of claim 1, wherein to receive the plurality of parameters including the free-form gesture path, the user interface module is to receive the free-form gesture path from a camera system.

7. The system of claim 6, wherein the camera system is incorporated into the user device.

8. The system of claim 6, wherein the camera system is separate from the user device.

9. The system of claim 1, wherein the free-form gesture path comprises a path in substantially two-dimensions.

10. The system of claim 1, wherein the free-form gesture path comprises a path in three-dimensions.

11. The system of claim 1, wherein to adjust the fitness routine for the user, the control module is to adjust at least one of: a resistance or an incline setting of an exercise apparatus used in the fitness routine.

12. The system of claim 1, wherein to analyze the free-form gesture path, the control module is to parameterize the free-form gesture path into a second coordinate system to produce a second parameterized free-form path; and wherein to use the path morphology to determine the navigation route, the control module is to transmit the second parameterized free-form path to a remote server to obtain the navigation route.

13. The system of claim 1, wherein to parameterize the free-form gesture path into the coordinate system to produce a parameterized free-form path, the control module is to use the length of the free-form path to parameterize a duration of an exercise session.

14. The system of claim 1, wherein to parameterize the free-form gesture path into the coordinate system to produce a parameterized free-form path, the control module is to use the shape of the free-form path in the x-z plane to parameterize a shape of the navigational route.

15. The system of claim 1, wherein to use the shape of the free-form path in the x-y plane to parameterize the intensity over time of an exercise session, the control module is to use a frequency or intensity of movement in the free-form path to parameterize the intensity over time.

16. A method of implementing a health application, the method comprising:
   receiving, at a user device, a plurality of parameters including a free-form gesture path, the free-form gesture path representing an air gesture performed by a user of the user device; and
   adjusting a fitness routine of the user based on the plurality of parameters,
   wherein adjusting the fitness routine for the user comprises:
      analyzing the free-form gesture path to obtain a path morphology, parameterizing the free-form gesture path into a coordinate system to produce a parameterized free-form path, and using the shape of the free-form path in the x-y plane to parameterize an intensity over time of an exercise session;
      using the path morphology to determine a navigation route and fitting the parameterized free-form path to a route with similar geographical topology; and
      presenting the navigation route to the user.

17. The method of claim 16, wherein adjusting the fitness routine for the user comprises adjusting at least one of:
   a resistance or an incline setting of an exercise apparatus used in the fitness routine.

18. The method of claim 16, wherein adjusting the fitness routine for the user comprises:
   analyzing the free-form gesture path to obtain a path morphology;
   using the path morphology to determine a navigation route; and
   presenting the navigation route to the user.

19. The method of claim 18, wherein analyzing the free-form gesture path comprises parameterizing the free-form gesture path into a coordinate system to produce a parameterized free-form path; and
   wherein using the path morphology to determine the navigation route comprises transmitting the parameterized free-form path to a remote server to obtain the navigation route.

20. The method of claim 16, wherein parameterizing the free-form gesture path into the coordinate system to produce a parameterized free-form path comprises using the length of the free-form path to parameterize a duration of an exercise session.

21. The method of claim 16, wherein parameterizing the free-form gesture path into the coordinate system to produce a parameterized free-form path comprises using the shape of the free-form path in the x-z plane to parameterize a shape of the navigational route.

22. At least one non-transitory machine-readable medium including instructions, which when executed by a machine, cause the machine to:
   receive, at a user device, a plurality of parameters including a free-form gesture path, the free-form gesture path representing an air gesture performed by a user of the user device; and
   adjust a fitness routine of the user based on the plurality of parameters,
   wherein the instructions to adjust the fitness routine comprise instructions to:
      analyze the free-form gesture path to obtain a path morphology, parameterize the free-form gesture path into a coordinate system to produce a parameterized free-form path, and use the shape of the free-form path in the x-v plane to parameterize an intensity over time of an exercise session;
      use the path morphology to determine a navigation route and fit the parameterized free-form path to a route with similar geographical topology; and
      present the navigation route to the user.

23. The at least one non-transitory machine-readable medium of claim 22, wherein adjusting the fitness routine for the user comprises adjusting at least one of: a resistance or an incline setting of an exercise apparatus used in the fitness routine.

24. The at least one non-transitory machine-readable medium of claim 22, wherein the instructions to analyze the free-form gesture path comprise instructions to parameterize the free-form gesture path into a coordinate system to produce a parameterized free-form path; and wherein the instructions to use the path morphology to determine the navigation route comprise instructions to transmit the parameterized free-form path to a remote server to obtain the navigation route.

* * * * *

UNITED STATES PATENT AND TRADEMARK OFFICE
CERTIFICATE OF CORRECTION

PATENT NO. : 10,289,206 B2  
APPLICATION NO. : 14/975362  
DATED : May 14, 2019  
INVENTOR(S) : Yuen et al.

Page 1 of 1

It is certified that error appears in the above-identified patent and that said Letters Patent is hereby corrected as shown below:

In Column 20, Line 7, in Claim 1, after "user", insert --,--

In Column 21, Line 31, in Claim 18, delete "morphology:" and insert --morphology;-- therefor In Column 22, Line 24, in Claim 22, delete "x-v" and insert --x-y-- therefor In Column 22, Line 39, in Claim 24, after "and", insert --¶--

Signed and Sealed this  
Sixteenth Day of June, 2020

Andrei Iancu  
*Director of the United States Patent and Trademark Office*